United States Patent
Afentakis et al.

(10) Patent No.: US 10,194,856 B2
(45) Date of Patent: Feb. 5, 2019

(54) MATRIX MULTI-SENSOR ARRAY

(71) Applicant: Sharp Laboratories of America (SLA), Inc., Camas, WA (US)

(72) Inventors: Themistokles Afentakis, Camas, WA (US); Anne Sledd, Vancouver, WA (US); Shivani Joshi, West Lafayette, IN (US)

(73) Assignee: Sharp Laboratories of America, Inc., Camas, WA (US)

( * ) Notice: Subject to any disclaimer, the term of this patent is extended or adjusted under 35 U.S.C. 154(b) by 154 days.

(21) Appl. No.: 15/098,377

(22) Filed: Apr. 14, 2016

(65) Prior Publication Data

US 2017/0172490 A1 Jun. 22, 2017

Related U.S. Application Data

(63) Continuation-in-part of application No. 14/977,910, filed on Dec. 22, 2015, now Pat. No. 9,949,683.

(51) Int. Cl.
*A61B 5/00* (2006.01)
*H01L 27/12* (2006.01)
*G01L 1/14* (2006.01)

(52) U.S. Cl.
CPC .......... *A61B 5/447* (2013.01); *A61B 5/6892* (2013.01); *G01L 1/146* (2013.01); *H01L 27/124* (2013.01);
(Continued)

(58) Field of Classification Search
None
See application file for complete search history.

(56) References Cited

U.S. PATENT DOCUMENTS

2007/0273394 A1 11/2007 Tanner et al.
2014/0116122 A1 5/2014 Lammel et al.
(Continued)

FOREIGN PATENT DOCUMENTS

| CN | 104523285 B | * | 9/2016 | ............... A61B 5/01 |
| JP | 2005108828 A | * | 4/2005 | |
| WO | WO2013144788 | | 10/2013 | |

OTHER PUBLICATIONS

R. Thomas, Does pressure cause pressure ulcers? Journal of the American Medical Directors Association, 11(6), 395-405, 2010.
(Continued)

*Primary Examiner* — Paresh H Patel
(74) *Attorney, Agent, or Firm* — ScienBiziP, P.C.; Alvin Koan (57) ABSTRACT

Disclosed herein are a circuit and a method for the electrical data read-out of a large-area sensor flexible circuit. This circuit incorporates sensing elements of two types, and is therefore used for the measurement of two physical metrics associated with the etiology of pressure ulcers, one of which might be pressure. The flexible circuit is large enough to cover the area(s) of the human body. The flexible circuit comprises electrically of the following components: (a) a passive or active matrix array, and (b) its scanning/read-out circuitry. The matrix array (a) comprises further of (i) two electrodes for the sensing of pressure in each sensing element (sensel) of the array, and (ii) two electrodes for the sensing of another metric (temperature, moisture, pH, etc.) in each sensel. One electrode is shared (common) between the first (i) and the second (ii) sensor in the sensel.

6 Claims, 8 Drawing Sheets

(52) U.S. Cl.
CPC .... *H01L 27/1255* (2013.01); *A61B 2562/029* (2013.01); *A61B 2562/0247* (2013.01); *A61B 2562/0252* (2013.01); *A61B 2562/046* (2013.01); *A61B 2562/066* (2013.01)

(56) References Cited

U.S. PATENT DOCUMENTS

| | | |
|---|---|---|
| 2014/0125359 A1 | 5/2014 | El-Gamam et al. |
| 2014/0198072 A1* | 7/2014 | Schuele .................. G06F 3/044 345/174 |

OTHER PUBLICATIONS

P. Slachta, Assessing risk of pressure- and moisture-related problems in long-term care patients, Wound Care Advisor, 2(3), 8-11, May-Jun. 2013.

http://www.healthleadersmedia.com/page-4/TEC-291902/Technology-Tackles-the-Pressure-Ulcer, May 7, 2013.
http://www.xsensor.com/Foresite, Jan. 22, 2015 (two pages).
http://www.bruinbiometrics.com/images/Brochures/SEMScannerDeviceBrochure-Distributors_RevB.pdf.
http://news.berkeley.edu/2015/03/17/smart-bandages-detect-bedsores/.
Takao Someya et al., "A large-area, flexible pressure sensor matrix with organic field-effect transistors . . . ", Proc. NAS of the USA, Jul. 6, 2004, vol. 101 No. 27, pp. 9966.
Takao Someya et al. "Conformable, flexible, large-area networks of pressure and thermal sensors with organic transistor active matrixes".
A. DeHennis et al., "An all-capacitive sensing . . . ", TRANSDUCERS, 12th International Conference on Solid-State Sensors, Actuators and Microsystems, vol. 2, p. 1860-1863, 2003.
Min-Xin Zhou, "A novel capacitive pressure sensor based on sandwich structures", Journal of Microelectromechanical Systems, vol. 14, Issue 6, pp. 1272-1282, 2005.

* cited by examiner

MATRIX MULTI-SENSOR ARRAY

RELATED APPLICATIONS

This application is a Continuation-in-part of an application entitled, DUAL-FUNCTION ACTIVE MATRIX SENSOR ARRAY, Ser. No. 14/977,910, filed Dec. 22, 2015, which is incorporated herein by reference.

BACKGROUND OF THE INVENTION

1. Field of the Invention

This invention generally relates to electronic array circuitry and, more particularly, to a sensor array with sensels able to monitor multiple environmental features.

2. Description of the Related Art

Early detection of pressure ulcers is extremely important in order to avoid the onset of potentially life-threatening and costly problems. Pressure ulcers are caused by pressure against the skin (typically in areas of bone protrusions), which leads to localized ischemia and, ultimately, tissue necrosis. In 2007, there were 5.2 million cases of pressure ulcers worldwide; 2.4 million cases (60,000 resulting in death) in the US alone. According to a recent study (5,000 hospitals from 2003 to 2005), pressure ulcers have one of the highest occurrence rates, along with failure to rescue and postoperative respiratory failure. Pressure ulcer etiology is mostly associated with the following three factors: (a) pressure, (b) temperature, and (c) moisture.

Sustained pressure, leading to reduced blood flow in the skin or deep muscle tissue, is considered the prevalent factor. A commonly used pressure level of 35 millimeters of mercury (mmHg) is considered a danger threshold, which can be as high as 200 mmHg over a bony prominence[1]. Also, friction, leading to skin tissue damage, and shear are implicated. Regarding temperature, in healthy individuals, a local increase of skin temperature results in increased blood flow. In risk patients, blood flow is not adequate to reduce temperature. A skin temperature increase by 1.2° C. over 24/48 hours increases the risk of forming a pressure ulcer. Finally, increased moisture levels (e.g. perspiration, incontinence) makes the skin more susceptible to damage, as increased skin pH expedites cell deterioration[2].

This problem is currently addressed by electronic devices that measure specific metrics on the surface of the body. The majority of devices (proposed or currently in the market) involve detecting high pressure points. This is achieved by obtaining two-dimensional pressure maps of part of, or of the entire area of the body in contact with the surface upon which it rests (seat, bed mattress, etc.). Representative commercially available systems of this type are the Wellsense MAP® system[3] (a Class I exempt device, costing about $4,000 per year and comprising of "thousands" or sensor points), and the XSensor flexible capacitive pad system[4] (Costing $9,500-$12,000 per sheet, with 1,664 sensor points).

Other options include (a) measuring the impedance of the human skin as a function of frequency (spectroscopic impedance), in order to detect the onset of sub-epidermal tissue necrosis[5], and (b) the capacitive measurement of the sub-epidermal skin layers to detect changes in sub-epidermal moisture (SEM), a biophysical marker of damaged tissue[6].

It would be advantageous if a low-cost device existed that made the monitoring and detections of pressure-related environmental factors more practical.

[1] R. Thomas, Does pressure cause pressure ulcers?, Journal of the American Medical Directors Association, 11(6), 395-405, 2010
[2] P. Slachta, Assessing risk of pressure- and moisture-related problems in long-term care patients, Wound Care Advisor, 2(3), 8-11, May/June 2013
[3] http://www.healthleadersmedia.com/page-4/TEC-291902/Technology-Tackles-the-Pressure-Ulcer
[4] http://www.xsensor.com/Foresite
[5] http://www.bruinbiometrics.com/images/Brocures/SEM-ScannerDeviceBrochure-Distributors_RevB.pdf
[6] http://news.berkeley.edu/2015/03/17/smart-bandages-detect-bedsores/

SUMMARY OF THE INVENTION

Disclosed herein are a circuit and a method for the electrical data read-out of a large-area sensor flexible circuit. This circuit incorporates sensing elements of two types, and is therefore used for the measurement of two physical metrics associated with the etiology of pressure ulcers, one of which is typically pressure. The flexible circuit is large enough to cover the surface area(s) of the human body upon which it rests (e.g., buttocks, back, or entire body). The flexible circuit comprises electrically of the following components: (a) a passive or active matrix array, and (b) its scanning/read-out circuitry. The matrix array (a) comprises further of (i) two electrodes for the sensing of pressure in each sensing element (sensel) of the array, and (ii) two electrodes for the sensing of another metric (temperature, moisture, pH, etc.) in each sensel. One electrode is shared (common) between the first (i) and the second (ii) sensor in the sensel. Therefore, a total of three electrodes are used to for the two sensing elements per sensel.

Scanning (read-out) of the array is accomplished by applying a voltage (or current) source between a specific column (common row) and row of the array, and measuring the current flow (or voltage across it). This may be an AC measurement (where and AC signal is applied and measured) or a DC measurement. Typically, a capacitive or inductive sensor requires an AC measurement, while a resistive sensor may be read with a DC measurement. There are several aspects of the circuit, depending on if the sensors (Sens1 and Sens2) are capacitive, resistive, or inductive sensors. Both sensors need not be of the same electrical type.

Accordingly, a method is provided for fabricating a matrix multi-sensor array. The method forms a bottom substrate. A bottom row layer includes a first film overlying the bottom substrate, and a plurality of bottom row electrodes overlying the first film. A first sensor sheet includes a first sensor layer overlying the bottom row layer, and a plurality of middle electrodes overlying a top surface of the first sensor layer. A second sensor sheet including a second sensor layer is formed overlying top surfaces of the middle electrodes and exposed top surfaces of the first sensor layer. The second sensor sheet also includes a plurality of top row electrodes overlying a top surface of the second sensor layer. A top substrate is formed overlying the top row electrodes and exposed surfaces of the second sensor layer. The crossings of the middle electrodes with the top and bottom row electrodes form a plurality of sensing elements (sensels), where each sensel includes a top passive sensor and a bottom passive sensor.

Typically, the bottom substrate, first film, first row electrodes, first sensor layer, middle electrodes, second sensor layer, top row electrodes, and top substrate are flexible materials. In one aspect, the top row electrodes are arranged to avoid overlap with top row electrodes, thus minimizing parasitic capacitance.

In another aspect, an active matrix is formed with a plurality of FET transistors overlying the first sensor sheet, one transistor per sensel. Each transistor in a column of sensels has a source terminal connected to a corresponding underlying middle electrode, a gate terminal, and a drain terminal. A plurality of control lines is formed orthogonal to the middle electrodes. Each control line is connected to the gate terminal of a corresponding underlying row of transistors. In this case, the second sensor sheet is formed overlying the control lines, transistors, top surfaces of the middle electrodes, and exposed top surfaces of the first sensor layer.

Additional details of the above-described method, a matrix multi-sensor array, and active multi-sensor array are provided below.

DETAILED DESCRIPTION

Figure 1:
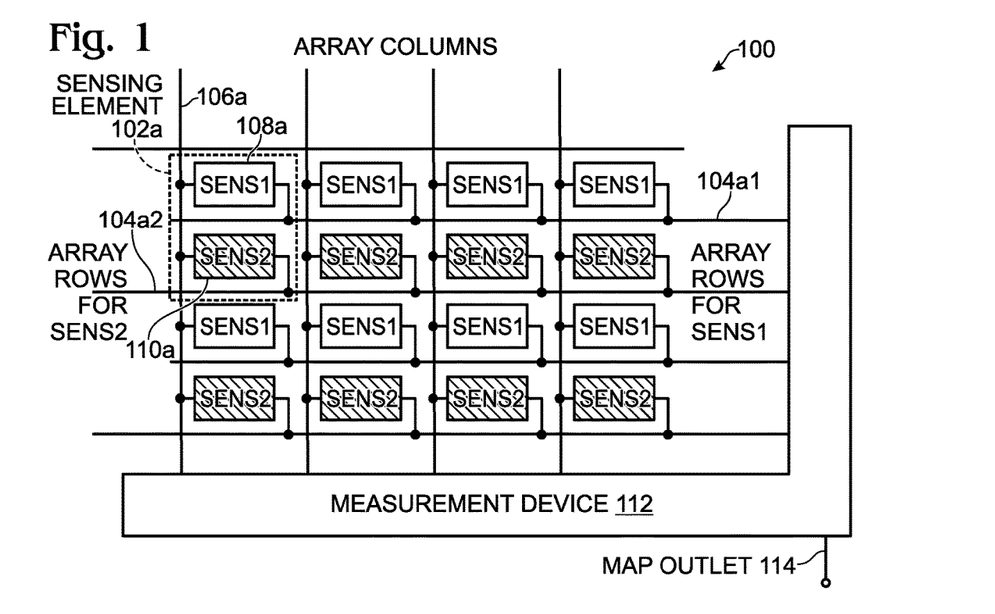
FIG. 1 is a schematic plan view of a matrix multi-sensor array.

FIG. 1 is a schematic plan view of a matrix multi-sensor array. The multi-sensor array 100 comprises a plurality of sensing elements (sensels). Each sensel, using sensel 102a as an example, comprises a middle electrode (line) 106a and two row electrodes (lines) 104a1 and 104a2. A first passive sensor (Sens1) 108a is connected between the middle electrode 106a and the first row electrode 104a1 to measure a first environmental condition. A second passive sensor (Sens2) 110a is connected between the middle electrode 106a and the second row electrode 104a2 to measure a second environmental condition different than the first environmental condition. A first terminal of the first sensor 108a and a first terminal of the second sensor 110a are connected to the middle electrode 106a. A second terminal of the first sensor 108a is connected to a first row electrode 104a1, and a second terminal of the second sensor 110a is connected to a second row electrode.

The first passive sensor 108a and the second passive sensor 110a each (independently) measure environmental conditions such as force, which may be normal, shear, or torque, pressure, humidity, temperature, moisture, chemicals, salinity, oxygen, shear, or pH. The first passive sensor 108a and the second passive sensor 110a may be parallel-plate or co-planar interdigitated electrode capacitors, metal-oxide-semiconductor (MOS) capacitors, parallel-plate or co-planar interdigital electrode resistors, or inductors. The first passive sensor 108a need not be the same type of device as the second passive sensor 110a. Further, the sensels need not be configured with the same types of devices. That is, the sensels need not be identical. Note: the array 100 is not limited to any particular number of sensels.

A measurement device 112 has an interface connected to the middle electrode and row electrodes of each sensel. The measurement device 112 injects a first signal between the middle electrode 106a and the first row electrode 104a1 and measures the first environmental condition by detecting a change in the first signal. When the measurement device 112 injects a second signal between the middle electrode 106a and the second row electrode 104a2, it measures the second environmental condition by detecting a change in the second signal. The first and second signals may be either alternating or direct current sources, and in one aspect, different current sources may be used. In this manner, the measurement device 112 determines the first environmental condition independent of second environmental condition measurements, and determines the second environmental conditions independent of first environmental condition measurements. The measurement device has an interface on line 114 (map output) to supply an environmental map or alarm signals. The measurement device may incorporate logic circuitry to enable alarm or mapping functions.

Figure 2:
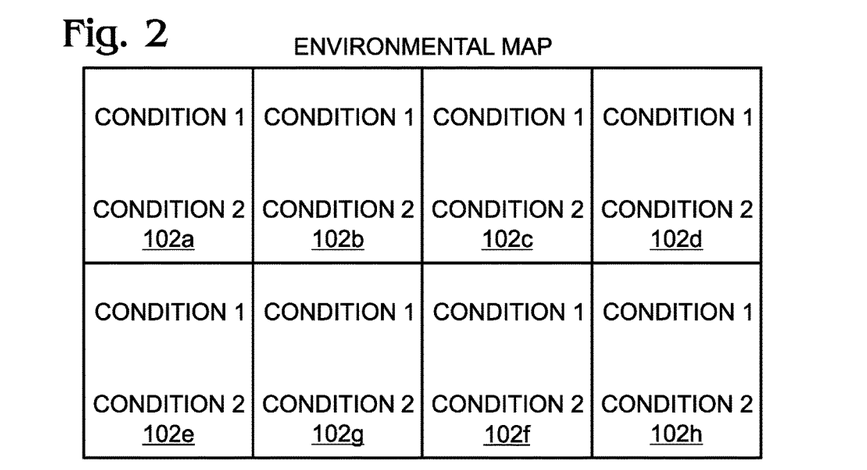
FIG. 2 depicts an environmental map such as might be obtained using the multi-sensor array of FIG. 1.

FIG. 2 depicts an environmental map such as might be obtained using the multi-sensor array of FIG. 1. The measurement device has a user output to supply a map of first and second environmental conditions, cross-referenced to sensel locations in the array.

Figure 3:
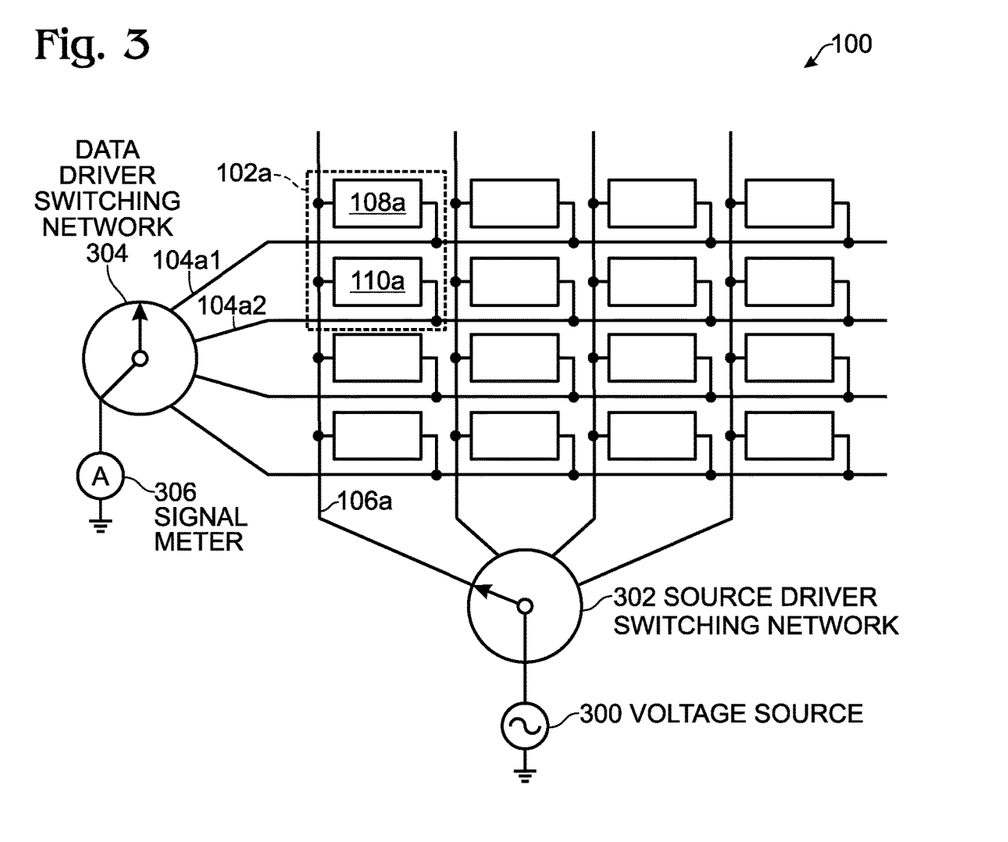
FIG. 3 is a plan view of the multi-sensor array of FIG. 1 showing additional details.

FIG. 3 is a plan view of the multi-sensor array of FIG. 1 showing additional details. In this example the measurement device comprises a signal generator enabled as an alternating current (AC) voltage source 300. A source driver switching network 302 selectively connects a middle electrode to the AC voltage source. Middle electrode 106a is shown connected. A data driver switching array 304 selectively connects a row electrode to an AC signal meter 306. As shown, the data driver switching network is connecting row electrode 104a1 to the signal meter 306. The combination of the source driver switching network 302 and data driver switching network 304 function to enable the measurement of selected passive sensors. As shown, sensor 108a is being measured. Again, it should be remembered that in some aspects a DC voltage source and corresponding signal meter may be used. Further, multiple type of signals or signal source may be used.

If AC signals are used, environmental conditions may be measured in response to detecting a change in the AC signal amplitude or a change in phase with respect to the input signal. The signal meter may therefore measure current, voltage, or phase. An AC impedance meter is able to make such a measurement. Alternatively, a network analyzer can be used. In one variation AC signals may be supplied at a plurality of frequencies, where each AC signal frequency has a predetermined amplitude and phase. The use of multiple frequencies may be advantageous if the highest sensitivities of RDs and the passive element impedance are at different frequencies. A calculating device (not shown) may be connected to the measurement equipment to supply alarms or to provide the environmental map depicted in FIG. 2.

Figure 4:
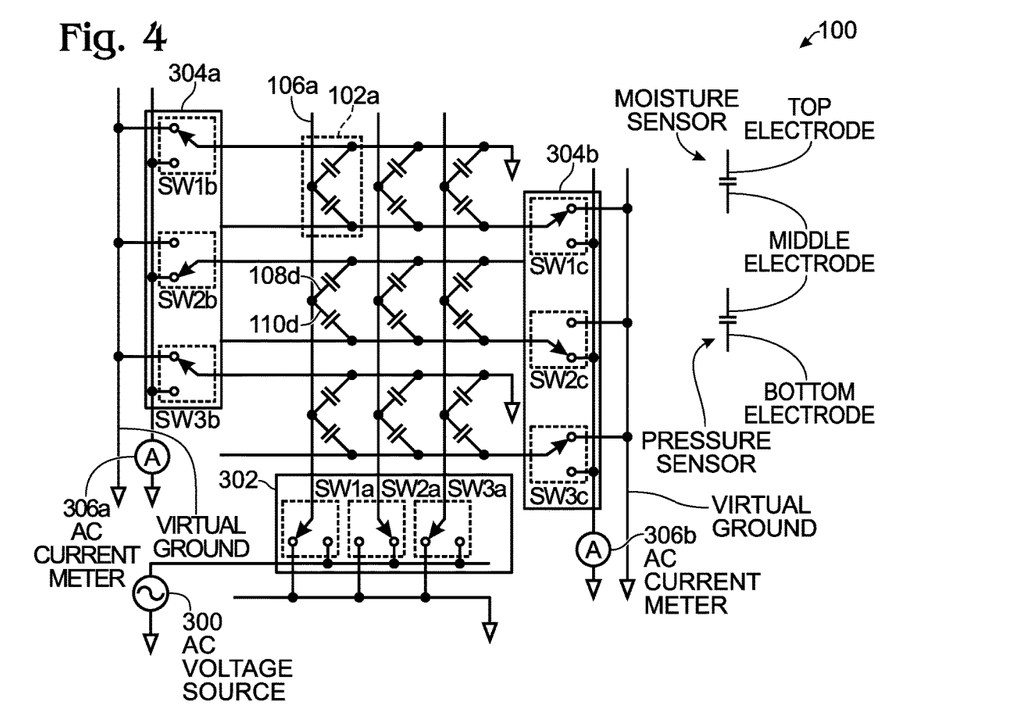
FIG. 4 is a plan view of the multi-sensor array of FIG. 1 enabled with two data driver switching networks and two signal meters.

FIG. 4 is a plan view of the multi-sensor array of FIG. 1 enabled with two data driver switching networks and two signal meters. Data driver switching network 304a selectively connects one set of row electrodes from each sensel to signal meter 306a, and data driver switching network 304b selectively connects to other set of row electrodes from each sensel to signal meter 306b. This arrangement permits two different sensels to be measured simultaneously. As shown, sensor 108d is being measured by signal meter 306a, and sensor 110d is being measured by signal meter 306b.

Figure 5:
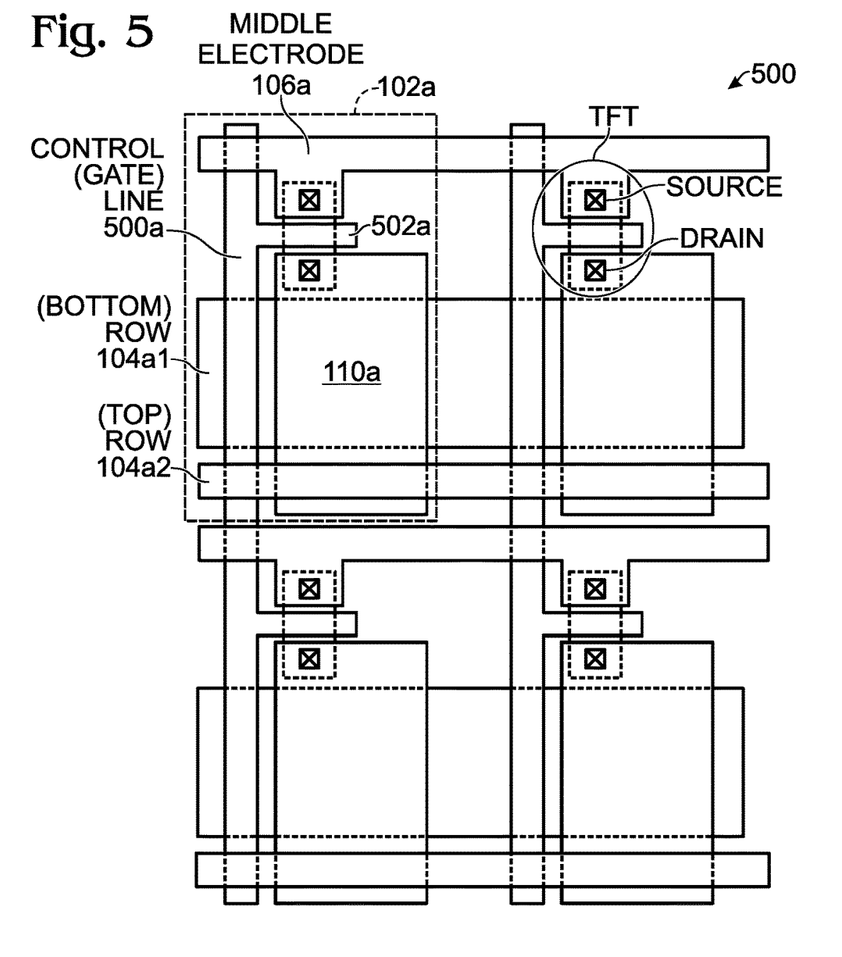
FIG. 5 is a plan view of an active matrix multi-sensor array.

FIG. 5 is a plan view of an active matrix multi-sensor array. In addition to the components described above, each sensel of the active matrix array 500 further comprises a control electrode (e.g., 500a), and a FET transistor (e.g., 502a). Using sensel 102a as an example, the FET transistor 502 has a gate connected to the control electrode 500a, a source connected to the middle electrode 106a, and a drain connected to the first terminal of the first passive sensor and to a first terminal of the second passive sensor 110a. Note: the first passive sensor 108a cannot be seen in this view because it underlies the second sensor 110a. The first passive sensor has a second terminal connected to the first (bottom) row electrode 104a1, and the second passive sensor 110a has a second terminal connected to the second (top) row electrode 104a2.

Figure 6:
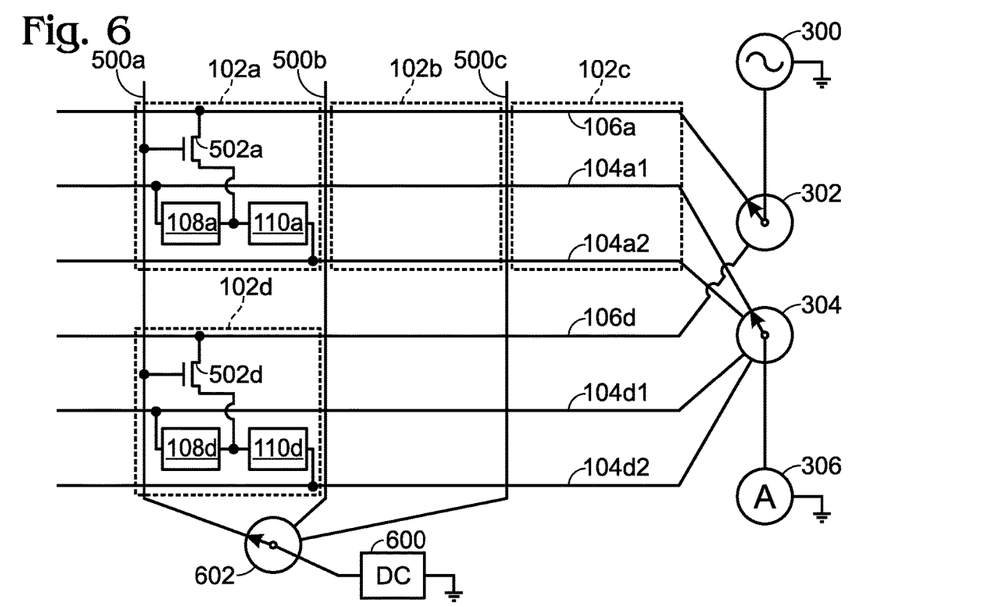
FIG. 6 depicts an exemplary measurement device that could be used with the active multi-sensor array of FIG. 5.

FIG. 6 depicts an exemplary measurement device that could be used with the active multi-sensor array of FIG. 5. The measurement device comprises a signal generator (in this example an AC voltage source) 300 and a source driver switching network 302 to selectively connect a middle electrode to the AC voltage source. A direct current (DC) source driver switching network 602 selectively connects a control line to the DC voltage source 600. A data driver switching network 304 selectively connects a row electrode to the signal meter (in this example an AC signal meter) 306. The combination of the source driver switching network 302, data driver switching network 304, and DC source driver switching network 602 function to enable the measurement of selected passive sensors.

Returning to FIG. 1, it can be seen that each sensel comprises of (a) one column (middle) electrode; (b) two row electrodes; (c) a pressure sensor (capacitive or resistive) between the column electrode and the first of the row electrodes, and (d) a sensor (for skin conductance, humidity, temperature, pH, etc.) between the column electrode and the second of the row electrodes. In order to minimize parasitic capacitance interference, the row electrodes that connect to the first sensor (Sens1) do not overlap with the row electrodes that connect to the second sensor type (Sens2).

Returning to FIG. 3, scanning (read-out) of the array is accomplished by applying a voltage (or current) source between a specific column (middle electrode) and row of the array, and measuring the current flow (or voltage across it). This may be an AC measurement (where and AC signal is applied and measured) or a DC measurement. Typically, a capacitive or inductive sensor requires an AC measurement, while a resistive sensor may be read with a DC measurement.

There are several aspects to the array, depending on the sensors (Sens1 and Sens2) used: capacitive, resistive, or inductive sensors. Both sensors need not be of the same electrical type. Typically, one of the two sensors is designed to measure pressure.

Figure 7:
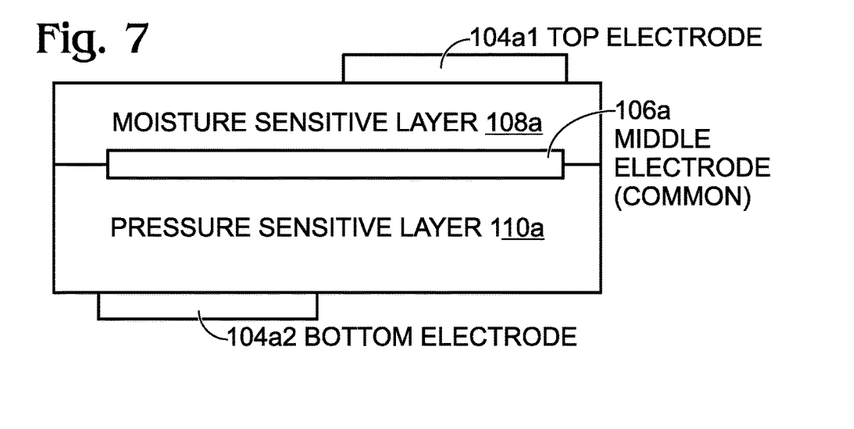
FIG. 7 is a partial cross-sectional view of a passive matrix sensel.

FIG. 7 is a partial cross-sectional view of a passive matrix sensel. In this example, moisture is measured by the first sensor 108a, but other sensitive layers (temperature, pH, and others) may be used. This schematic is simplified, in that only critical layers are shown. Depending on the type/construction of the individual sensing layers, additional layers may be inserted for mechanical support, to prevent diffusion of moisture, to provide thermal or electrical isolation, etc.

For example, the top electrode 104a1 may be made of a metal such as aluminum, copper, silver, gold, or other, with a typical thickness in the range of 10 nm (nanometers)-10 µm (microns). The first sensor 108a may measure conditions such as moisture, temperature, or pH. This layer might be inorganic or an organic polymer, typically ranging in thickness from 0.5 µm to a 1 mm. This layer might respond to changes in the physical parameter it is made to detect, by a change in its resistivity, electric, or magnetic permittivity. It might be desirable to incorporate nanoparticles, nanotubes, or other structures into this film, to enhance its sensitivity.

The middle electrode 106a may be made of a metal such as aluminum, copper, silver, gold, or other, with a typical thickness in the range of 10 nm-10 µm. The second sensor 110a may be a pressure-sensitive layer, which may be an inorganic film or organic polymer or foam. This layer may range in thickness from 1 µm to 10 mm. This layer may be responsive to variations in pressure (e.g., normal or shear), measured by a change in its resistivity, electric, or magnetic permittivity. It might be desirable to incorporate nanoparticles, nanotubes, or other structures into this film, to enhance its sensitivity. The bottom electrode 104a2 may be made of a metal such as aluminum, copper, silver, gold, or other, with a typical thickness in the range of 10 nm-10 µm.

Figure 8:
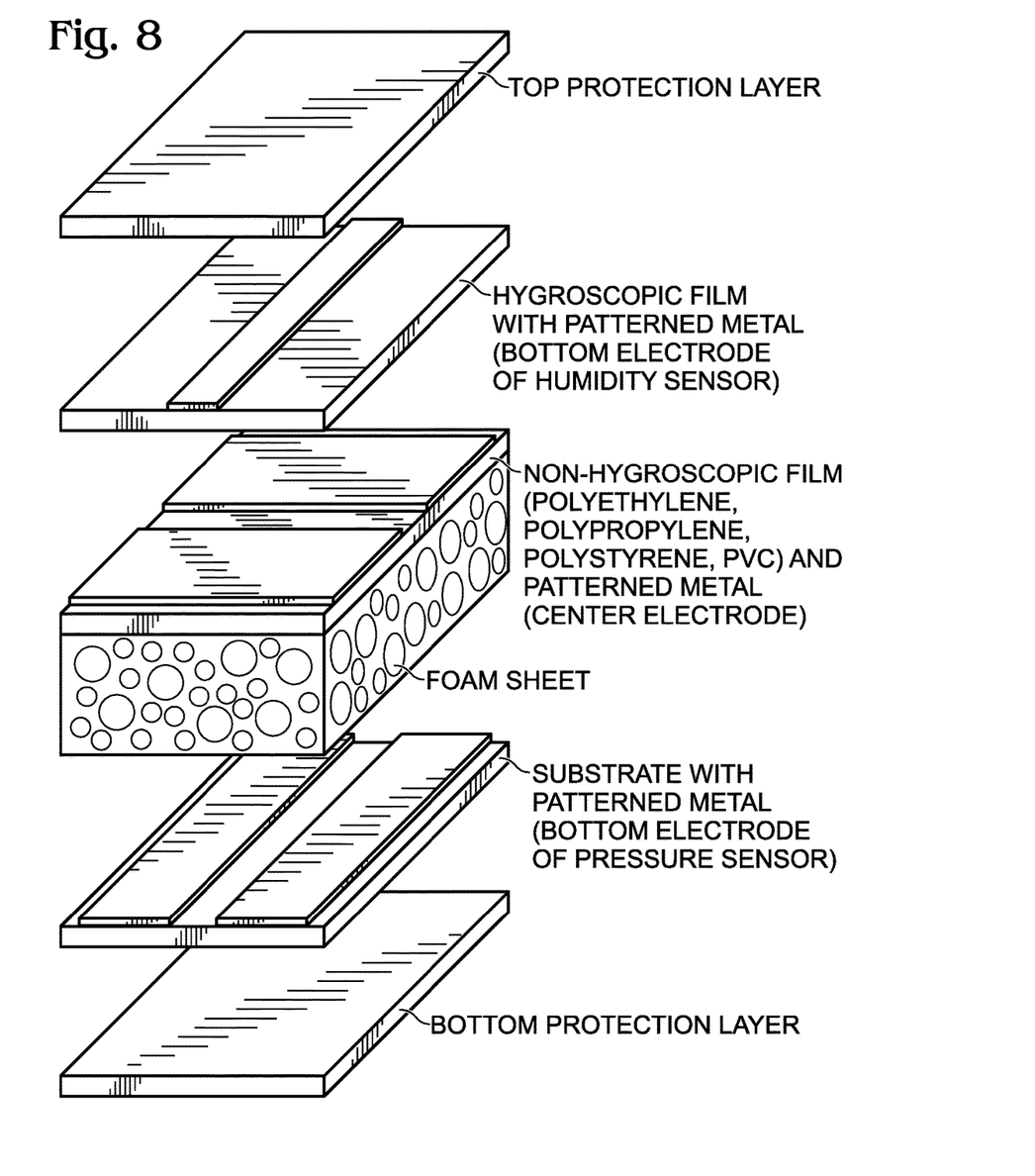
FIG. 8 is a schematic cross-section showing the passive matrix sensel in greater detail.

FIG. 8 is a schematic cross-section showing the passive matrix sensel in greater detail. The layers are not drawn to scale. In this aspect, a capacitive moisture sensor is the first (top) sensor, and a capacitive pressure sensor is the second (bottom) sensor. A hygroscopic polymer (such as polyimide, bis(benzo cyclobutene) (BCB), cellulose and poly-N-epoxypropylcarbazole (PEPC), cellulose acetate butyrate (CAB), poly(methyl methacrylate) (PMMA), Polydimethylphosphazene (PDMP), or others might be used for such a capacitive moisture sensor. Alternatively, a resistive moisture sensing layer (4-vinylpyridine (4-vp) with butyl methacrylate (BuMA), 4-Vinylbenzyl dimethyl 2-(dimethylamino) ethyl ammonium chloride, methyl methacrylate (MMA) and [3-(methacrylamino)propyl] trimethyl ammonium chloride (MAPTAC), Polyamidoamine (PAMAM) dendrimers, Poly-dimethylphosphazene (PDMP), 6,13-bis(triisopropylsilylethynyl) pentacene (TIPS pentacene), or similar might be used.

The patterned metal electrode (top electrode) on the hygroscopic film might be a thin Au or Ag layer, typically 1-100 nm, in order to allow the diffusion of water molecules. The pressure-sensitive layer forms the dielectric material of the bottom sensor (pressure-sensitive capacitive sensor). This layer is engineered to mechanically deform (compress) under pressure applied normal to the sensor surface. It might typically comprise of an elastomer (silicone, polyurethane etc. based), which can incorporate nanoparticles, nanotubes, or air inclusions (foam), in order to enhance its sensitivity to pressure. This layer might range in thickness from 1 µm to 10 mm, depending on its Young modulus.

One or more metals for the electrode might be replaced with other conductive inorganic or organic compounds (e.g. graphene, metal, or carbon nanoparticle in a polymer, or paper matrix, and others). A non-hygroscopic layer is incorporated into the structure, below the middle electrode to prevent moisture from diffusing into the pressure-sensitive layer and the rest of the structure.

The structure is completed by the bottom electrode, and top and bottom protection layers, which provide chemical and mechanical protection to the structure. All layers at the thicknesses involved can be flexible, therefore the complete structure can flex and follow the contours of the human body and/or of the surface it rests upon.

Figure 9A:
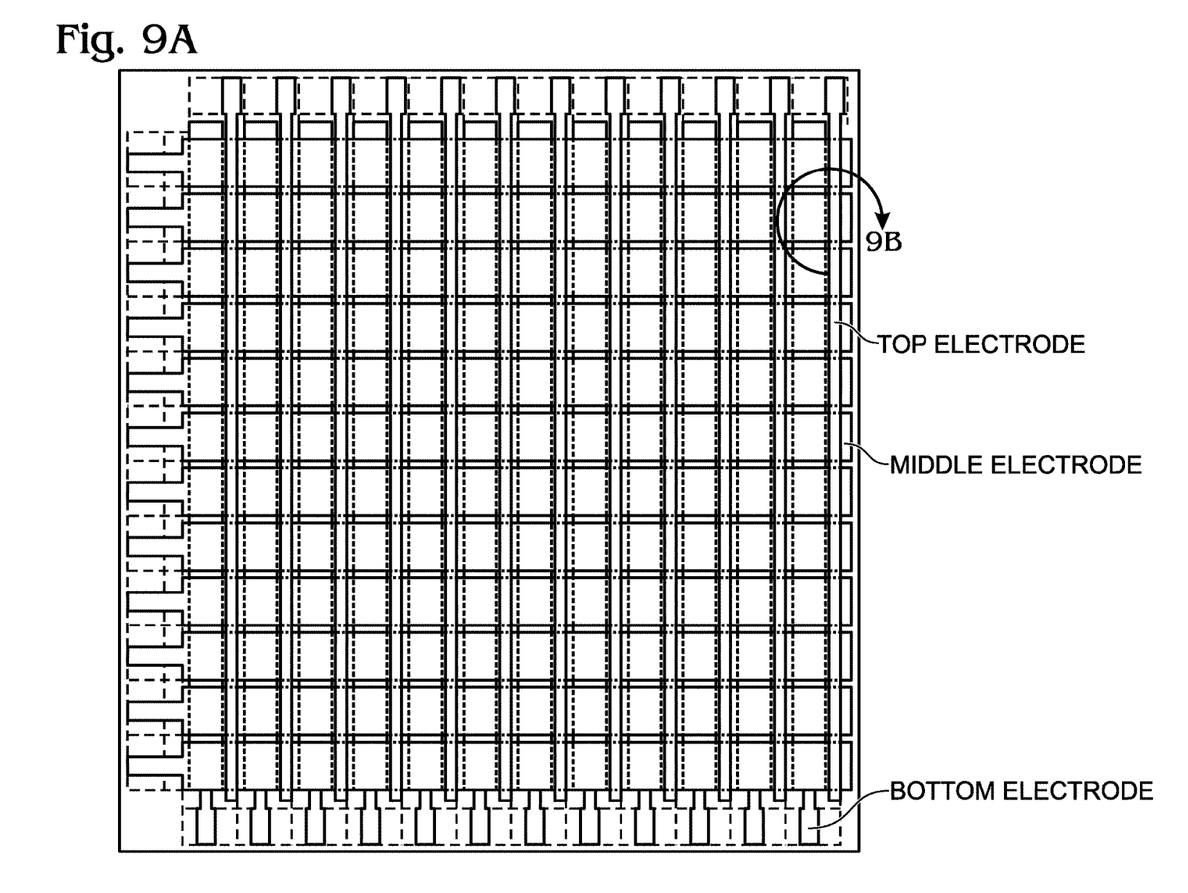
FIG. 9A depicts a plan view of an exemplary array, with a detail shown in FIG. 9B, and a schematic cross-section shown in FIG. 9C.
Figure 9B:
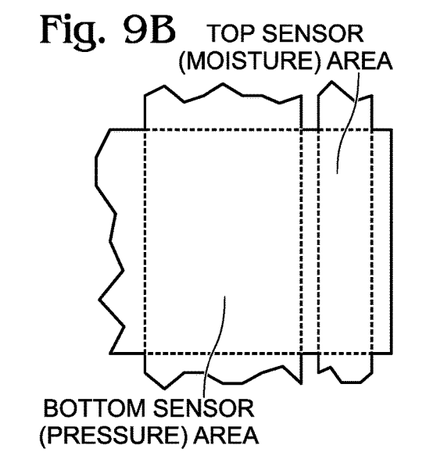
Figure 9C:
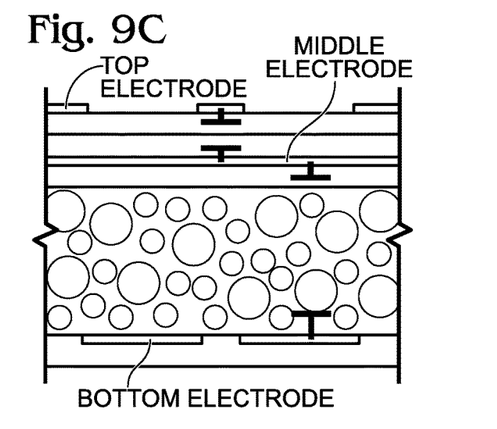

FIG. 9A depicts a plan view of an exemplary array, with a detail shown in FIG. 9B, and a schematic cross-section shown in FIG. 9C. In order to detect high-pressure points, the sensel may need to be of a size in the range of 0.3×0.3 $cm^2$ to 3×3 $cm^2$. The areas of the pressure and the moisture sensor need not be identical. As seen in FIGS. 9B and 9C, the area of the bottom pressure sensor element is greater, in order to increase it capacitance, which is typically low due to the small dielectric constant of most pressure-sensitive polymers, and the thickness of the polymer dielectric. The top and the bottom electrodes are non-overlapping, in order to minimize the parasitic capacitive coupling between them.

Returning to FIG. 4, an exemplary sensor read-out scheme is shown for the matrix dual-sensor array. A 3×3 sensel array is shown. In one aspect, each sensel utilizes two capacitive sensors (moisture and pressure). The array is driven by three groups of external switching circuitry. These are used to switch ON/OFF the group of top electrodes, middle electrodes, and bottom electrodes, so that all lines in each of these groups are at ground potential, except one.

An AC voltage line is connected one-at-a-time to a middle electrode line, via switches SW1a-SW3a. At the same time, only one of the top electrode lines is connected to an AC current meter, via switches SW1b-SW3b. This way, the AC impedance of only one element (the moisture sensor 108d) is measured. Likewise, only one of the bottom electrode lines is connected to an AC current meter, via switches SW1c-SW3c. This way, the AC impedance of only one element (the pressure sensor 110d) is measured. In another embodiment of this driving scheme (FIG. 3), a single AC current meter may be used, with the addition of a switch that connects it either to the top-electrode, or to the bottom-electrode switches.

As shown in FIGS. 5 and 6, active devices (typically n-channel or p-channel MOSFET switches) may be used to modify the passive array to create an active-matrix. Such an embodiment provides the inherent active-matrix advantages of better signal-to-noise ratio, and lower cross-talk. This is achieved by increasing design complexity (MOSFET switches in every sensel, and at an additional control line). However, such a tradeoff is typically acceptable, for high resolution and/or high accuracy applications. Alternatively but not shown, switching may be performed using more than one FET per sensel as is well known in the design of display device pixels.

Figure 10:
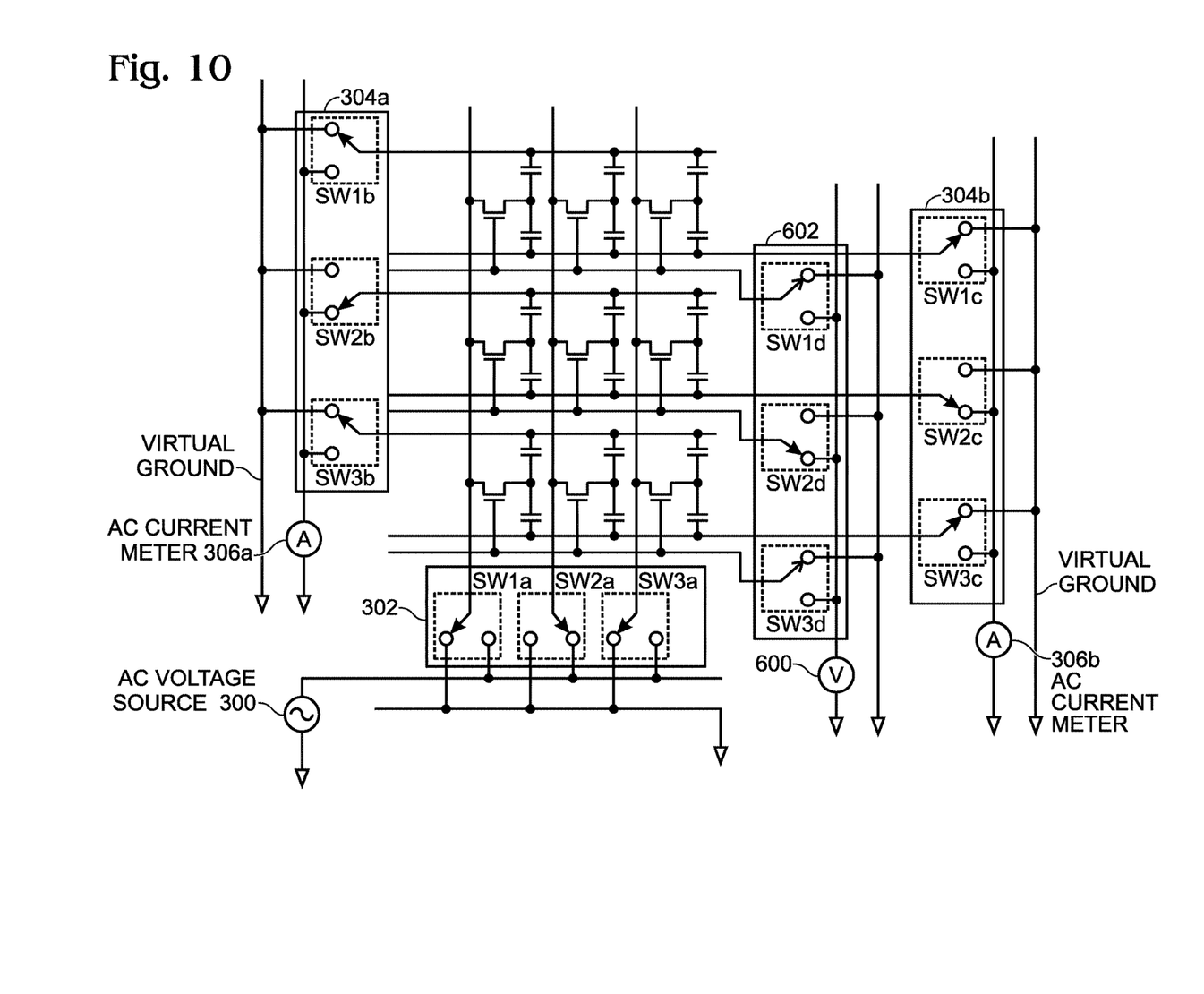
FIG. 10 is a schematic drawing depicting an exemplary sensor read-out scheme for the active-matrix dual-sensor 3×3 sensel array.

FIG. 10 is a schematic drawing depicting an exemplary sensor read-out scheme for the active-matrix dual-sensor 3×3 sensel array. For example, each sensel may utilize two capacitive sensors (moisture and pressure). The array is driven by four groups of external switching circuitry. These are used to switch ON/OFF the group of top electrodes, middle electrodes, bottom electrodes, and transistor switch gate lines, so that all lines in each of these groups are at ground potential, except one.

The array is read by activating one row at a time; this is achieved using the gate driver circuit 602, comprising switches SW1d-SW3d. Shown for n-type MOSFETs, the gate lines of all rows are held low, except one (the middle one in the schematic), which is biased high. This, turns all MOSFETs in that array line ON. While the gate line in held high, an AC voltage line is connected to one middle electrode (applied at the drain of the MOSFET switches), one-at-a-time, via switches SW1a-SW3a (302). When the MOSFET switch is ON, this AC signal is effectively applied to the anodes of the sensor capacitors.

At the same time, the read-out switches SW1b-SW3b (304a for one type of sensor) and SW1c-SW2 (304b for the other type of sensor) are activated, probing the same line that the gate line switches (SW1d-SW3d) have activated. This way, the AC impedances associated with only one element (the two capacitive sensors in the center of the 3×3 array) are measured. This measurement can take place simultaneously (i.e., SW2b and SW2c are simultaneously turned to the AC current meter path), or one impedance is read first (e.g. SW2b turns to the AC current meter and then to ground), before reading the other impedance.

In another embodiment (FIG. 6), a single AC current meter may be used, with the addition of a switch that connects it either to the top-electrode, or to the bottom-electrode switches.

Figure 11:
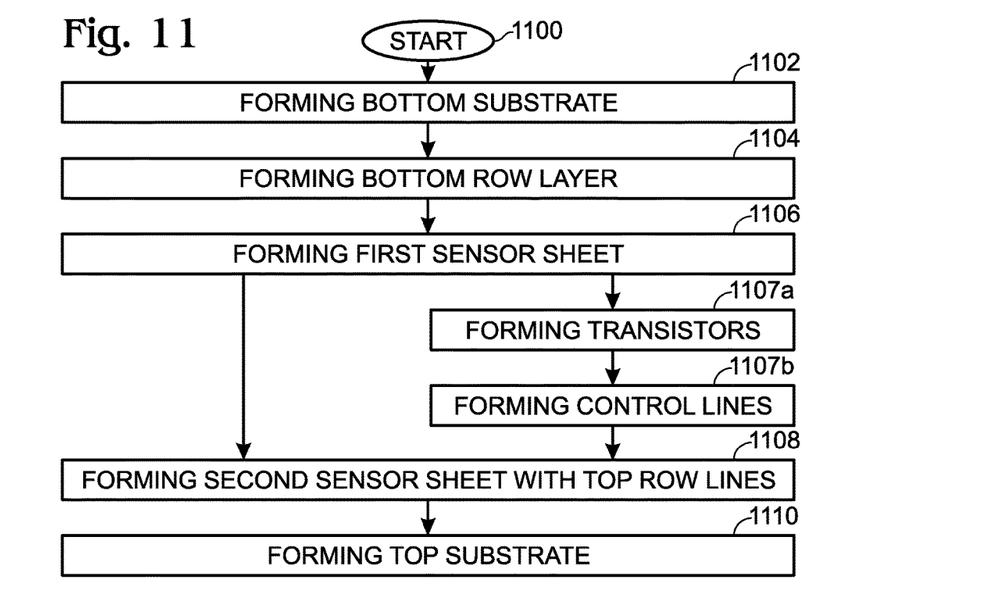
FIG. 11 is a flowchart illustrating a method of fabricating a matrix multi-sensor array.

FIG. 11 is a flowchart illustrating a method of fabricating a matrix multi-sensor array. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. Generally however, the method follows the numeric order of the depicted steps. The method starts at Step 1100.

Step 1102 forms a bottom substrate. Step 1104 forms a bottom row layer including a first film overlying the bottom substrate, and a plurality of bottom row electrodes overlying the first film. Step 1106 forms a first sensor sheet including a first sensor layer overlying the bottom row layer, and a plurality of middle electrodes overlying a top surface of the first sensor layer. In the case of a passive matrix, the bottom row and middle electrodes are orthogonally aligned. Step 1108 forms a second sensor sheet including a second sensor layer overlying top surfaces of the middle electrodes and exposed top surfaces of the first sensor layer. The second sheet also includes a plurality of top row electrodes overlying a top surface of the second sensor layer. In the case of a passive matrix, the top row electrodes are orthogonal to the middle electrodes. Step 1110 forms a top substrate overlying the top row electrodes and exposed surfaces of the second sensor layer. The crossings of the middle electrodes with the top and bottom row electrodes form a plurality of sensels, where each sensel includes a top passive sensor and a bottom passive sensor. In one aspect, forming the second sensor sheet in Step 1108 includes arranging the top row electrodes to avoid overlap with top row electrodes.

Typically, the bottom substrate, first film, first row electrodes, first sensor layer, middle electrodes, second sensor layer, top row electrodes, and top substrate are flexible materials. For example, the top row electrodes and bottom row electrodes may be made from materials such as aluminum, copper, silver, gold, graphene, metal or carbon particles in a polymer matrix, and metal or carbon particles in a paper matrix. The first and second sensor layers may be made from materials with capacitive characteristics such as a hygroscopic polymer, including polyimide bis(benzo cyclobutene) (BCB), cellulose and poly-N-epoxypropylcarbazole (PEPC), cellulose acetate butyrate (CAB), poly(methyl methacrylate) (PMMA), and polydimethylphosphazene (PDMP). Alternatively, the first and second sensor layers may be materials with resistive characteristics such as (4-vinylpyridine (4-vp) with butyl methacrylate (BuMA), 4-vinylbenzyl dimethyl 2-(dimethylamino)ethyl ammonium chloride, methyl methacrylate (MMA) and [3-(methacrylamino)propyl] trimethyl ammonium chloride (MAPTAC), polyamidoamine (PAMAM) dendrimers, polydimethylphosphazene (PDMP), and 6,13-bis(triisopropylsilylethynyl) pentacene (TIPS) pentacene. In one aspect, at least one of the first and second sensor layers are a non-hygroscopic material.

If the first and second sensor layers are pressure-sensitive dielectric materials, they may be a silicon or polyurethane elastomer, or an elastomer further comprising nanoparticles, nanotubes, and air inclusions.

In an active matrix aspect of the method, Step 1107a forms a plurality of FET transistors overlying the first sensor sheet, at least one transistor per sensel. Each transistor in a column of sensels has a source terminal connected to a corresponding underlying middle electrode, a gate terminal, and a drain terminal. Step 1107b forms a plurality of control lines orthogonal to the middle electrodes. Each control line is connected to the gate terminal of a corresponding underlying row of transistors. Then, forming the second sensor sheet in Step 1108 includes forming the second sensor sheet overlying the control lines, transistors, top surfaces of the middle electrodes, and exposed top surfaces of the first sensor layer.

Passive and active multi-sensor arrays have been provided. Examples of particular hardware elements and exemplary environmental conditions have been presented to illustrate the invention. However, the invention is not limited to merely these examples. Although the invention has primarily been presented as a device for monitoring only two conditions in the interest of simplicity, it should be understood that a sensel may include multiple TFTs and/or multiple passive elements to monitor more than two conditions. Likewise, different types of two-element (or multi-element) sensels may be arranged in an array for a similar purpose. Other variations and embodiments of the invention will occur to those skilled in the art.

We claim:

1. A matrix multi-sensor array comprising:
   a plurality of sensing elements (sensels), each sensel comprising:
   a middle electrode;
   two row electrodes;
   a first passive sensor connected between the middle electrode and a first row electrode to measure a first environmental condition;
   a second passive sensor connected between the middle electrode and a second row electrode to measure a second environmental condition different than the first environmental condition;
   a control electrode;
   a FET transistor having a gate connected to the control electrode, a source connected to the middle electrode, and a drain connected to a first terminal of the first passive sensor and to a first terminal of the second passive sensor;
   the first passive sensor having a second terminal connected to the first row electrode; and,
   the second passive sensor having a second terminal connected to the second row electrode; and
   a measurement device comprising:
   a signal generator;
   a source driver switching network to selectively connect the middle electrode to the signal generator;
   a direct current (DC) voltage source;
   a DC source driver switching network to selectively connect a control line to the DC voltage source;
   a data driver switching network to selectively connect a row electrode to a signal meter; and,
   wherein the combination of the source driver switching network, data driver switching network, and DC source driver switching network function to enable the measurement of selected passive sensors.

2. The matrix multi-sensor array of claim 1 wherein the first and second passive sensors each measure environmental conditions selected from a group consisting of force (normal, shear, or torque), pressure, humidity, temperature, moisture, chemicals, salinity, oxygen, shear, and pH.

3. The matrix multi-sensor array of claim 1 wherein the first and second passive sensors are each selected from the group consisting of a parallel-plate or co-planar interdigitated electrode capacitors, metal-oxide-semiconductor (MOS) capacitors, parallel-plate or co-planar interdigital electrode resistors, and inductors.

4. The matrix multi-sensor array of claim 1, the measurement device further comprising:
   an interface connected to the middle electrode and row electrodes of each sensel;
   wherein the measurement device injects a first signal between the middle electrode and the first row electrode and measures the first environmental condition by detecting a change in the first signal; and
   wherein the measurement device injects a second signal between the middle electrode and the second row electrode and measures the second environmental condition by detecting a change in the second signal.

5. The matrix multi-sensor array of claim 4 wherein the measurement device has a user output to supply a map of first and second environmental conditions, cross-referenced to sensel locations in the array.

6. The matrix multi-sensor array of claim 4 wherein the measurement device determines the first environmental condition independent of second environmental condition measurements, and determines the second environmental conditions independent of first environmental condition measurements.

* * * * *